United States Patent [19]

Doorakian et al.

[11] 4,266,079
[45] May 5, 1981

[54] PROCESS FOR PREPARING TETRAHYDROCARBYLPHOSPHONIUM BICARBONATE SALTS

[75] Inventors: George A. Doorakian, Bedford; Lawrence G. Duquette, Maynard; John F. Arnett, Newton, all of Mass.

[73] Assignee: The Dow Chemical Company, Midland, Mich.

[21] Appl. No.: 91,280

[22] Filed: Nov. 5, 1979

[51] Int. Cl.$^3$ ............................................... C07F 9/54
[52] U.S. Cl. .................................................. 568/11
[58] Field of Search ..................... 260/606.5 F; 568/11

[56] References Cited

U.S. PATENT DOCUMENTS

| 3,193,529 | 7/1965 | Oxenrider | 260/606.5 F |
| 4,048,141 | 9/1977 | Doorakian et al. | 260/606.5 F |

OTHER PUBLICATIONS

Denney et al., J. Org. Chem., vol. 27, pp. 3404–3409 (1962).
Kosolapoff et al., Organic Phosphorus Compounds, vol. 2, pp. 200–202, Wiley–Interscience, N. Y. (1972).

*Primary Examiner*—Helen M. S. Sneed
*Attorney, Agent, or Firm*—Michael L. Glenn

[57] ABSTRACT

Certain tetrahydrocarbylphosphonium bicarbonate salts are produced by reacting a trihydrocarbyl(hydrocarbylcarboxymethyl)phosphonium hydroxide inner salt with water. For example, methyl tri-n-butylphosphonium bicarbonate salt was prepared in quantitative yields by heating tri-n-butylcarboxymethylphosphonium hydroxide inner salt in an aqueous methanol solution at 100° C. for 3 hours.

12 Claims, No Drawings

PROCESS FOR PREPARING TETRAHYDROCARBYLPHOSPHONIUM BICARBONATE SALTS

BACKGROUND OF THE INVENTION

1. Field of the Invention

This invention relates to the preparation of a tetrahydrocarbylphosphonium bicarbonate salt from a trihydrocarbyl(hydrocarbylcarboxymethyl)phosphonium hydroxide inner salt.

2. Description of the Prior Art

The preparation and reactions of certain phosphobetaines were described by Denney et al., *J. Org. Chem.*, Vol. 27, pp. 3404–3409 (1962). This reference discloses that triphenyl(carboxyethyl)phosphonium hydroxide inner salt, a so-called phosphobetaine, is soluble in water, but does not disclose the occurrence of any reaction between these components elucidated in the determination of the chemical properties of these compounds.

SUMMARY OF THE INVENTION

It has now been discovered that certain tetrahydrocarbylphosphonium bicarbonate salts are prepared in a process comprising reacting (a) a trihydrocarbyl(hydrocarbylcarboxymethyl)phosphonium hydroxide inner salt represented by the formula

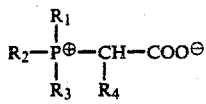

in which $R_1$–$R_3$ are each independently hydrocarbyl or inertly-substituted hydrocarbyl radicals having from 1 to about 20 carbon atoms, and $R_4$ is phenoxy, phenyl, hydrogen or an alkyl having from 1 to about 20 carbon atoms, with (b) water. The tetrahydrocarbylphosphonium bicarbonate salts are extremely useful catalysts for promoting the reaction between (1) vicinal epoxides and (2) phenols or carboxylic acids or anhydrides. These novel salts can be represented by the formula

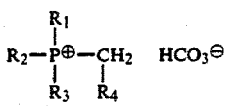

DETAILED DESCRIPTION OF THE INVENTION

The reactants in the instant process are known classes of compounds. Trihydrocarbyl(hydrocarbylcarboxymethyl)phosphonium hydroxide inner salts and methods for their preparation are described in U.S. Pat. No. 4,048,141, the relevant portions of which are incorporated herein by reference. The compound of formula I can be conveniently prepared by reacting a trihydrocarbyl phosphine with a substituted α-chloroacetic acid represented by the formula

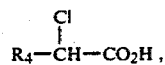

wherein $R_4$ is as previously mentioned, followed by treatment with a base. This method of preparation is particularly advantageous where $R_4$ is H. A salt of a substituted or unsubstituted α-chloroacetic acid can be employed in the aforementioned method in place of the α-chloroacetic acid, in which case no base treatment is necessary. Preferably, this salt is a sodium salt.

It is essential in this preparation that the phosphobetaine reactant (depicted in formula I) contain as little residual halogen ion from the starting materials as possible (preferably less than 1 percent by weight), as halogen ions can produce undesirable by-products during the reaction of the phosphobetaine. The use of a commercial ion-exchange resin in the tertiary amine or hydroxide forms as the base in the preparation of the compound of formula I minimizes the presence of halogen ions in the product. Alternatively, the phosphobetaine solution can be subjected to electrodialysis to reduce the presence of these halide ions to acceptable levels.

When $R_4$ is an alkyl, phenyl or phenoxy group, the above-described method of preparation of compounds represented by formula I is frequently of low yield. A potentially more efficient synthetic route in these instances is to react a $C_1$–$C_4$ alkyl ester of a substituted α-haloacetic acid with a trihydrocarbyl phosphine in an inert liquid reaction medium such as diethyl ether. The resulting tetrahydrocarbylphosphonium halide (wherein one of the hydrocarbyl groups is a methylenecarboxylate ester) is reacted with dilute hydrochloric acid to hydrolyze the ester in the following manner (wherein $R_1$–$R_3$ are as aforementioned; $R_4$ is alkyl, phenyl or phenoxy, $R_5$ is $C_1$–$C_4$ alkyl and X is a halide ion):

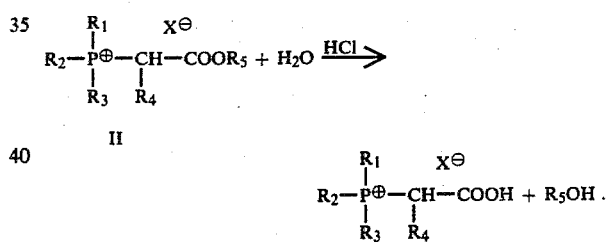

The reaction is conducted at elevated temperatures to distill off the alkanol by-product and drive the reaction to substantial completion. The compound represented by formula III is then contacted with a commercial ion-exchange resin (in the hydroxide or tertiary amine form) to produce a compound corresponding to formula I.

The hydrocarbyl moieties, $R_1$–$R_3$, borne by the compound of formula I, are univalent hydrocarbon radicals which may be the same or different and which may bear substituents inert in the instant reaction. For example, $R_1$–$R_3$ can be alkyl (such as methyl, ethyl, propyl, dodecyl), aryl (such as phenyl), alkaryl (such as a dodecylbenzene radical), aralkyl (such as benzyl, phenylethyl), hydroxyalkyl or cyanoalkyl. Preferably, $R_1$–$R_3$ are each independently phenyl or a $C_1$ to $C_{12}$ alkyl group and more preferably are each independently phenyl or a $C_1$ to $C_4$ alkyl group. Most preferably $R_1$–$R_3$ are each phenyl or n-butyl. $R_4$ is preferably methyl or hydrogen, most preferably hydrogen.

The stoichiometry of the subject reaction requires at least one mole of water per mole of the compound of formula I. An excess of water is preferred to insure complete reaction of the phosphobetaine reactant.

The reaction can be conducted either neat or in a liquid inert organic diluent. By the term "inert" is meant, once again, inert in the instant process. Suitable diluents include water, water-miscible lower alkanols ($C_1$–$C_4$) and mixtures of such lower alkanols with aromatic hydrocarbon solvents, such as benzene or toluene. Preferably, the instant process is conducted with no diluent other than the reactants themselves (i.e., neat) or methanol is employed as a diluent. The instant reaction can also be conducted with the reactant of formula I in the solid phase and the water reactant present in the vapor phase or adsorbed on the solid phosphobetaine reactant. The phosphobetaine reactant is hygroscopic. However, reaction in the liquid phase is preferred.

The order of addition or method of contacting the reactants is not critical and may be varied to convenience. Substantially any reaction temperature from about 20° to about 125° C. can be used to advantage, preferably about 50° to about 100° C. Typically, the reaction rate will be more rapid at higher temperatures within the aforementioned ranges. Lower reaction temperatures than the foregoing are operable, but require uneconomically long reaction times.

The reaction time for the rearrangement to the phosphonium bicarbonate salt is dependent upon the identity of $R_1$–$R_3$ borne by the reactant represented by formula I. For example, at 25° C. a methanol solution containing an equivalent quantity of the triphenylcarboxymethylphosphonium hydroxide inner salt and water is quantitatively converted to the corresponding bicarbonate salt after 240 hours. In contrast, the analogous tri-n-butyl derivative is stable in an aqueous methanol solution at 25° C. for more than 6 months.

The atmosphere above the reactants is desirably inert in the reaction. Where the water reactant is adsorbed on the solid compound of formula I, the reaction should be conducted at a pressure of less than 20 millimeters of mercury. The pressure above the reactants in the liquid phase is not critical, so long as the reactants are maintained in intimate contact.

In the liquid phase reaction, the pH of the reaction medium should be at least about 7, preferably 8 or greater.

Experimental:

The following examples are illustrative of the present invention. All parts and percentages are by weight, unless otherwise specified.

EXAMPLE 1

A solution of 647.25 grams (6.85 moles) of monochloroacetic acid in 161.84 grams of water was added dropwise over a period of 1.5 hours to a stirred solution of 1400.0 grams (6.776 moles) of tri-n-butyl phosphine in 74.7 grams of water under a nitrogen atmosphere. The temperature of the reaction mixture was controlled so as not to exceed 35° C. The reaction mixture was stirred for an additional 30 minutes at 25°–35° C. and then was heated to 85° C. for 2 hours in the presence of air. The reaction yielded 2242.0 grams of a clear, colorless solution, which was found by infrared spectroscopy and proton, phosphorus-31 and carbon-13 nuclear magnetic resonance spectroscopy to contain 88.8 percent tri-n-butyl(carboxymethyl)phosphonium chloride.

A portion of the above-described aqueous product solution containing 610.0 grams (1.825 moles) of tri-n-butyl(carboxymethyl)phosphonium chloride was added with stirring to 164.0 grams (5.12 moles) of methanol. This methanol solution was then contacted immediately with an excess of a commercial ion-exchange resin either as the hydroxide or the tertiary amine form at 20° C. to produce a solution pH greater than 7. The solution was filtered to remove the ion-exchange resin. A proton magnetic resonance analysis of the filtrate confirmed that virtually quantitative conversion to the tri-n-butyl(carboxymethyl)phosphonium hydroxide inner salt had occurred. The methanol solution of this phosphobetaine was distilled at 50° C. at reduced pressure (0.1 millimeter mercury). The resulting viscous, hygroscopic liquid was heated at 25° C. under vacuum for 2 weeks to produce a colorless crystalline solid, which was identified as substantially pure tri-n-butylmethylphosphonium bicarbonate salt by nuclear magnetic resonance spectroscopy, infrared spectroscopy and elemental analysis.

EXAMPLE 2

Solid monochloroacetic acid (76.0 grams, 0.80 mole) was added rapidly at 25° C. to a stirred solution of triphenylphosphine (104.0 grams, 0.40 mole) in 120 milliliters of toluene under a nitrogen atmosphere. After 30 minutes, the reaction mixture was slowly heated to 42° C. to dissolve the monochloroacetic acid and was stirred vigorously at this temperature for about 2 hours. The stirring was stopped and the mixture separated into two phases. After 12 hours at 25° C. the bottom phase crystallized to a white solid, which was collected, washed with diethyl ether and air dried to yield 125.0 grams of a white solid product. The infrared and phosphorus-31 and proton nuclear magnetic spectrums and the elemental analysis of this product determined its identity to be triphenylcarboxymethyl phosphonium chloride chloroacetic acid complex.

The white solid product described immediately above was dissolved in an 81.0 gram solvent mixture of 95 percent methanol and 5 percent water. This aqueous methanol solution was then percolated slowly through a column containing an excess of a commercial ion-exchange resin in the tertiary amine form to produce a solution having a pH greater than 7.0. The methanol solvent was distilled at 0° C. at reduced pressure to yield a white solid product, which was then washed with diethyl ether and air dried. This white solid was identified by conventional methods of analysis as the triphenyl(carboxymethyl)phosphonium hydroxide inner salt.

The triphenyl(carboxymethyl)phosphonium hydroxide inner salt (75 grams) in a 366 gram solution of 95 percent methanol and 5 percent water was heated at 100° C. for 30 minutes. The methanol solvent is distilled at 25° C. under reduced pressure to yield 79 grams of a white solid. The product is identified by proton, carbon-13 and phosphorus-31 nuclear magnetic resonance and infrared spectroscopy as methyltriphenylphosphonium bicarbonate salt.

Utility:

To a reaction vessel equipped with stirring means and temperature indication and recording means was charged 6.6 grams of the diglycidyl ether of bisphenol A (DGEBA) having an epoxy equivalent weight of 187, 3.40 grams of bisphenol A and 0.0066 gram (0.1 part per hundred of resin) of triphenylmethylphosphonium bicarbonate salt at room temperature. The stirred mixture was heated to 150° C. and thereafter allowed to freely exotherm with no external heat applied. After the temperature of the mixture had peaked, heating was resumed for 2 additional hours to maintain a temperature of 180° C.

The observed epoxy content of the resin product determined by conventional wet analysis technique was 2.20 percent. The observed epoxy content was slightly greater than the theoretical epoxy content of 2.15 percent. A substantially linear epoxy resin of excellent color was provided.

This reaction demonstrates the utility of tetrahydrocarbylphosphonium bicarbonate salts as catalysts in the preparation of epoxy resins.

What is claimed is:

1. A process for preparing a tetrahydrocarbylphosphonium bicarbonate salt comprising reacting (a) a trihydrocarbyl(hydrocarbylcarboxymethyl)phosphonium hydroxide inner salt represented by the formula

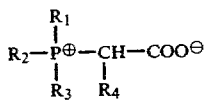

in which $R_1$-$R_3$ are each independently hydrocarbyl or inertly-substituted hydrocarbyl radicals having from 1 to 20 carbon atoms, and $R_4$ is phenoxy, phenyl, hydrogen or an alkyl having 1 to 20 carbon atoms with (b) water, so as to prepare a phosphonium bicarbonate salt represented by the formula

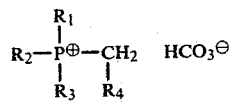

2. The process defined by claim 1 wherein the molar ratio of (b)/(a) is at least 1.

3. The process defined by claim 1 in which the reaction is conducted in an inert organic diluent.

4. The process defined by claim 3 in which the inert organic diluent is a lower alkanol having from 1 to 4 carbon atoms.

5. The process defined by claim 4 in which the inert organic diluent is methanol.

6. The process defined by claim 1 in which the reaction is conducted neat.

7. The process defined by claim 1 in which $R_1$-$R_3$ are each independently phenyl or a $C_1$ to $C_{12}$ alkyl group.

8. The process defined by claim 1 in which $R_1$-$R_3$ are each independently phenyl or a $C_1$ to $C_4$ alkyl group.

9. The process defined by claim 1 in which $R_1$-$R_3$ are each phenyl or n-butyl.

10. The process defined by claim 1 in which the reaction temperature is from about 20° to about 125° C.

11. The process defined by claim 2 wherein $R_1$-$R_3$ are each phenyl or n-butyl and the reaction is conducted in a methanol diluent at a temperature of from about 50° to about 100° C.

12. The process defined in claim 1 wherein reactant (a) contains less than 1 percent by weight of halide ion contaminants.

* * * * *